(12) United States Patent
Brizius et al.

(10) Patent No.: US 8,785,679 B2
(45) Date of Patent: Jul. 22, 2014

(54) HYDROPHILIC BIOCIDAL COATINGS

(71) Applicant: Empire Technology Development LLC, Wilmington, DE (US)

(72) Inventors: Glen Leon Brizius, Augusta, GA (US); Phillip Kent Montgomery, Arden, NC (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/881,540

(22) PCT Filed: Dec. 10, 2012

(86) PCT No.: PCT/US2012/068720
§ 371 (c)(1),
(2), (4) Date: Apr. 25, 2013

(65) Prior Publication Data
US 2014/0163136 A1    Jun. 12, 2014

(51) Int. Cl.
| | | |
|---|---|---|
| C07F 9/09 | (2006.01) |
| C07C 229/08 | (2006.01) |
| C07C 229/02 | (2006.01) |
| C07C 279/26 | (2006.01) |
| C07C 279/00 | (2006.01) |
| C01G 31/02 | (2006.01) |
| C01G 29/00 | (2006.01) |
| C01G 28/02 | (2006.01) |
| C09D 5/14 | (2006.01) |
| C09D 5/16 | (2006.01) |

(52) U.S. Cl.
USPC .............. 562/24; 562/11; 562/564; 562/575; 564/233; 564/236; 564/240; 556/76; 423/594.17; 106/15.05; 106/18.31; 106/18.32; 523/122

(58) Field of Classification Search
USPC .............. 562/11, 24, 575, 564; 564/233, 236, 564/240; 556/76; 423/594.17; 106/15.05, 106/18.31, 18.32; 523/122
See application file for complete search history.

(56) References Cited

U.S. PATENT DOCUMENTS

| | | | |
|---|---|---|---|
| 4,178,323 A | 12/1979 | Chattha | |
| 4,373,009 A | 2/1983 | Winn | |
| 4,759,872 A | 7/1988 | Marx et al. | |
| 4,906,237 A | 3/1990 | Johansson et al. | |
| 5,246,739 A | 9/1993 | Lin | |
| 5,324,731 A * | 6/1994 | Kaddurah-Daouk et al. | 514/275 |
| 5,874,025 A | 2/1999 | Heuer et al. | |
| 5,931,994 A | 8/1999 | Mateo Herrero | |

(Continued)

FOREIGN PATENT DOCUMENTS

WO    WO 97/00613    1/1997

OTHER PUBLICATIONS

Sergelius, Biochimica et Biophysica Acta-Biomembranes, 2013, vol. 1828, p. 785-791.*
Beatty, Nature, 1959, vol. 183, p. 591.*

(Continued)

Primary Examiner — Fereydoun G Sajjadi
Assistant Examiner — Amy C Bonaparte
(74) Attorney, Agent, or Firm — Pepper Hamilton LLP

(57) ABSTRACT

Hydrophilic, biocidal coating compositions and methods to make and use the compositions are disclosed. The coatings include compounds with quaternary amine polyethylene glycol groups and polyaminoalkyl biguanide groups as substituents. The compounds when incorporated in paints provide hydrophilic, self-cleaning and biocidal property to the coating.

19 Claims, 1 Drawing Sheet

(56) References Cited

U.S. PATENT DOCUMENTS

| | | | |
|---|---|---|---|
| 6,072,015 | A | 6/2000 | Bolle et al. |
| 6,231,651 | B1 | 5/2001 | Schultz et al. |
| 7,297,206 | B2 | 11/2007 | Naruse et al. |
| 8,409,627 | B2 | 4/2013 | Richardson et al. |
| 2004/0089196 | A1 | 5/2004 | Anderson et al. |
| 2007/0104766 | A1 | 5/2007 | Wang et al. |
| 2008/0308423 | A1 | 12/2008 | Slater |
| 2009/0149673 | A1 | 6/2009 | Zhang et al. |
| 2009/0203795 | A1 | 8/2009 | Yu |
| 2010/0261807 | A1 | 10/2010 | Laine et al. |
| 2012/0148751 | A1 | 6/2012 | Herdt et al. |

OTHER PUBLICATIONS

International Search Report and Written Opinion for PCT/US2012/068720 dated Mar. 1, 2013.
Allen et al., The response of *Escherichia coli* to exposure to the biocide polyhexamethylene biguanide, *Microbiology* (2006), 152:989-1000.
Amelotti et al., Experimental evaluation of insecticidal paints against *Triatoma infestans* (Hemiptera: Reduviidae), under natural climatic conditions, *Parasites & Vectors* (Jul. 8, 2009), 2:30, pp. 1-6.
Ansorg et al., Inhibition of the anti-staphylococcal activity of the antiseptic polihexanide by ucin, *Arzneimittelforschung* (2003), 53(5):368-371 (Abstract).
Biocides, http://www.lenntech.com/biocides.htm, (Printed from Internet Jul. 1, 2012).
Block, Disinfection, Sterilization, and Preservation, Lippincott Williams & Wilkins, Fifth Edition (Dec. 15, 2000).
Cooper, Will the world starve without pesticides?, A Publication of the Northwest Coalition for Alternatives to Pesticides, *Journal of Pesticide Reform*, (1991), 11(2):1-40.
Dean, Lange's Handbook of Chemistry, 7$^{th}$ Anniversary Edition, McGraw-Hill Professional; 15$^{th}$ Edition (Oct. 30, 1998).
Forest Products Laboratory, Listing of Publications, http://www.fpl.fs.fed.us/products/publications/several_pubs.php?grouping_id=100&header_id=p (Printed from internet Apr. 25, 2013).
Freeman et al., Past, Present, and Future of the Wood Preservation Industry, *Forest Products Journal* (Oct. 3002), 53(10):8-15.
Graf, Bunzalkonium chloride as a preservative in nasal solutions: re-examining the data, *Respiratory Medicine* (2001), 95:728-733.
Hexane, http://en.wikipedia.org/wiki/Hexane (Printed from Internet Apr. 3, 2013).
Hydrophilic vs. hydrophobic. The meaning of contact angle, SuperHydroPhobic Coating, http://superhydrophobiccoating.com/hydrophilic-hydrophobic-8/ (Printed Coating, from Internet Mar. 15, 2003).
Katz et al., Chemistry and toxicology of building timbers pressure-treated with chromated copper arsenate: a review, *Journal of Applied Technology* (2005), 25:1-7.
Marple et al., Safety review of benzalkonium chloride used as a preservative in intranasal solutions: An overview of conflicting data and opinions, *Otolaryngology—Head and Neck Surgery* (2004), 130(1):131-141.
Material Safety Data Sheet—Acetic Acids MSDS, http://sciencelab.com/xMSDS-Acetic_acid-9922769, (Jun. 9, 2012).
Material Safety Data Sheet—Dimethyl Carbonate MSDS, http://www.sciencelab.com/msds.php?msdsId=9923808, (Jun. 9, 2012).
Menzel, Ozone: An overview of its toxicity in man and animals, *Journal of Toxicology and Environmental Health* (Oct. 20, 2009), 13(2-3):181-204 (Abstract).
Petrillo et al., A General Preparation of Protected Phosphoamino Acids, *Org. Lett.* (Feb. 22, 2012), 14(5):1206-1209 (Abstract).
Phytoremediation: Using Plants to Clean Up Soils, http://www.ars.usda.gov/is/AR/archive/jun00/soil0600.htm?pf=1 (Printed from Internet Apr. 25, 2013).
Prashad et al., Practical Synthesis of 3-Carboxy-(2R)-[[hydroxy[(tetradecyl)oxy] phosphinyl]oxy]- *N,N,N*-trimethyl-1-propanaminium Hydroxide Inner Salt (CPI975): A Carnitine Palmitoyltransferase I Inhibitor, *Org. Proc. Res. Dev.* (Sep. 17, 2002), 6(6):773-776 (Abstract).
Rowell, Chemical Modification of Wood, Chapter 22, pp. 673-691 (http://1128.104.77.228/documnts/pdf2007/fpl_2007_rowel1005.pdf) (Printed from Internet Apr. 25, 2013).
Shieh et al., Nucleophilic Catalysis with 1,8-Diasabicyclo[5.4.0]under-7-ene (DBU) for the Esterification of Carboxylic Acids with Dimethyl Carbonate, *J. Org. Chem.* (Mar. 1, 2002), 67:2188-2191.
Tundo et al., The Chemistry of Dimethyl Carbonate, *Acc. Chem. Res.* (Jun. 5, 2002), 25(9):706-716.
Volatile Organic Compounds, Health Effects Fact Sheet (Nov. 2000), http://www.epa.gov/ttncaaa1/t1/fact_sheets/voc_exemp01011309.pdf.
Wade, A Treatise on the Dry Rot in Timber, General Books (Jul. 24, 2010).
Wakamiya et al., Preparations of N$^{\alpha}$-Fmoc-*O*-[(Benzyloxy)hydroxyphosphinyl] β-Hydroxy α-Amino Acid Derivatives, *Bulletin of the Chemical Society of Japan* (Jun. 20, 1996), 69(2):465-468 (Abstract).
Wakamiya et al., An Efficient Procedure for Solid-Phase Synthesis of Phosphopeptides by the Fmoc Strategy, *Chemistry Letters* (Apr. 19, 2006), 23(6):1099-1102 (Abstract).
Water, http://en.wikipedia/wiki/Water (Printed from Internet Apr. 3, 2013).
Whitten et al., Chemistry, 10$^{th}$ Edition, Cengage Learning (2009).
Wormell, Chromated Copper Arsenate (CCA), Pesticides: Regulating Pesticides, http://www.epa.gov/oppad001/reregistration/cca (Printed from Internet Apr. 25, 2013).

\* cited by examiner

HYDROPHILIC BIOCIDAL COATINGS

CLAIM OF PRIORITY

This application is a U.S. national stage filing under 35 U.S.C. §371 of International Application No. PCT/US2012/068720 filed on Dec. 10, 2012 entitled "Hydrophilic Biocidal Coatings", which is incorporated herein by reference in its entirety.

BACKGROUND

Coatings and paints are routinely used to beautify and protect substrates. The most simple coatings and paints are made of a polymer (the binder) in a solvent (the vehicle), which is commonly called a lacquer. Paints and coatings modify the appearance of an object by adding color, gloss, or texture, and by blending with or differentiating from a surrounding environment. For example, a surface that is highly light scattering can be made glossy by the application of a paint that has a high gloss. Conversely, a glossy surface can be made to appear flat. Thus, the painted surface is hidden, altered, and ultimately changed in some manner by the presence of the coating. In addition, paints also protect the surface from the surrounding elements and prevent or reduce the corrosive process.

Paints and coatings, while protecting the substrate from external environment, can themselves get dirty over time. The dirt can dull the coating by increasing light scattering or by modifying the color of the coating. Dirt can also affect the durability of a paint. A surface with a hydrophilic coating, however, would allow water to spread out in a thin layer, sweeping dirt off the surface as the water thins out and trickles away. This type of "self-cleaning" behavior is advantageous to an exterior paint, as it keeps the coating clean without requiring extensive cleaning by the customer. A hydrophilic surface would allow water to sheathe over the surface and either solvate or even carry away the dirt molecules.

Biofouling represents a significant problem for any wetted surface or structure, and may result in interference with the normal use and condition of the surface or structure. Such interference can lead to premature break down of wetted structures and surfaces, and can have significant economic implications to a number of industries. Biofouling also results in decoloration of paint surfaces due to the compounds secreted by microorganisms and algae, and affect paint durability. Constant exposure of a surface or a structure to water results in the deposition of dissolved organic material as a thin film and recruitment of bacterial colonies, resulting in formation of a biofilm. Upon attaching to the surface, the bacteria release substances that further provide mechanical stability to the biofilm, through electrostatic forces such as hydrogen bonds and van der Walls interactions. As the attached bacterial cells begin to multiply, the biofilm thickens, further aiding attachment of larger organisms, such as plants, algae or animals. These larger organisms colonize the biofilm coated surfaces and secrete compounds, such as glycoproteins, which allows these organisms to become nearly permanently attached to a surface. Accordingly, there is a need to develop coatings with biocidal, hydrophilic and self-cleaning properties.

SUMMARY

This disclosure is about compounds that provide biocidal, hydrophilic and self-cleaning properties when incorporated in paints and coatings. In an embodiment, a compound is of formula I wherein E is phosphorus, bismuth, arsenic or vanadium; $R_1$ is wherein A is alkyl, substituted alkyl, cycloalkyl, heteroalkyl, aryl, heteroaryl or substituted aryl;

$R_2$ is —$CH_2$— or —CH(—$CH_3$)—;
$R_3$ is wherein n is an integer from 2 to 20; and
$R_4$ is H, vinyl, propenyl, butenyl, pentenyl, or hexenyl.

In another embodiment, a method of making a biocidal compound may include: (a) contacting an inorganic halide with an end-capped polyethylene glycol and an amino acid to form an intermediate compound; and (b) contacting the intermediate compound with a poly aminoalkyl biguanide to form the biocidal compound.

In an additional embodiment, a method of making a paint polymer may include: (a) contacting an inorganic halide with an end-capped polyethylene glycol and an amino acid to form an intermediate compound; (b) contacting the intermediate compound with a polyaminoalkyl biguanide to form a biocidal compound; (c) contacting the biocidal compound with an alkene to form a monomer; and (d) incorporating the monomer into a polymer to form the paint.

In a further embodiment, a coating composition may include an acrylic polymer comprising a monomeric unit of formula I

I wherein E is phosphorus, bismuth, arsenic or vanadium;
R$_1$ is wherein A is alkyl, substituted alkyl, cycloalkyl, heteroalkyl, aryl, heteroaryl or substituted aryl;
R$_2$ is —CH$_2$— or —CH(—CH$_3$)—;
R$_3$ is wherein n is an integer from 2 to 20; and
R4 is vinyl, propenyl, butenyl, pentenyl, or hexenyl.

In another embodiment, an article may be coated with a coating, wherein the coating includes an acrylic polymer comprising a monomer of formula I as described herein.

DETAILED DESCRIPTION

This disclosure is not limited to the particular systems, devices and methods described, as these may vary. The terminology used in the description is for the purpose of describing the particular versions or embodiments only, and is not intended to limit the scope.

"Alkyl" refers to monovalent saturated aliphatic hydrocarbyl groups having from 1 to 24 carbon atoms and preferably 1 to 10 carbon atoms. This term includes, by way of example, linear and branched hydrocarbyl groups such as methyl (—CH$_3$), ethyl (—CH$_2$CH$_3$), n-propyl (—CH$_2$CH$_2$CH$_3$), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—) and t-butyl ((CH$_3$)$_3$C—).

"Aryl" refers to an aromatic carbocyclic group from 5 to 14 carbon atoms having a single ring (e.g., benzo) or multiple condensed rings (e.g., diphenyl, naphthyl or anthryl) which condensed rings may or may not be aromatic.

"Heteroaryl" refers to an aromatic group that contains at least one heteroatom selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom.

"Heteroalkyl" refers to alkyl groups in which one or more C atoms are substituted by oxygen, nitrogen, sulfur or combinations thereof.

"Cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain 3 to 15, 3 to 10, 3 to 8, 3 to 6, 4 to 6, 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like.

"Substituted alkyl" refers to an alkyl described herein in which one or more hydrogen atoms attached to carbon of the alkyl is replaced by another group, such as halogen, aryl, substituted aryl, cycloalkyl, substituted cycloalkyl, and combinations thereof. Suitable substituted alkyls include, for example, benzyl and trifluoromethyl.

"Substituted aryl" refers to aryl described herein in which one or more hydrogen atoms attached to any carbon atoms is replaced by one or more functional groups such as alkyl, substituted alkyl, cycloalkyl, substituted cycloalkyl, heterocycloalkyl, substituted heterocycloalkyl, halogen, halogenated alkyl (e.g., CF$_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Examples of substituted aryls include perfluorophenyl, chlorophenyl, 3,5-dimethylphenyl, 2,6-diisopropylphenyl and the like.

As paints and coatings become covered and contaminated with unwanted substances, the appearance of the coated object often changes in undesirable ways. It is often expensive, time consuming and hazardous to clean the coated surface, and the detergents, surfactants, fragrances, alkali, lime, and/or other chemicals used to clean the surface make their way into the environment where they can potentially cause damage. Thus, it is desirable to have a coating with a hydrophilic surface that keeps dirt from sticking to the surface, is self-cleaning, and contains environmental friendly chemicals.

The durability of paints is also influenced by biofouling, and paint additives and polymers with anti-biofouling or biocidal properties may be used to overcome these issues. However, there are marked distinctions between the requirements for biocides in different environments, such as antifungal agents in house paints, algicides for fresh water structures, and antifouling agents for marine structures exposed to sea water flora and fauna. As is known, the mildew or fungus which grows on house paints and the like, utilizes the paint medium as a nutrient, or in some cases, the underlying substrate, such as wood, as the nutrient. The mycelia and fruiting bodies of the fungi contact or penetrate the paint film and thus, through intimate contact with any fungicides in the film, the fungi are destroyed. In the case of marine structures, such as coatings on the surface of a boat's hull, the anti-biofouling agents act at the surface of the paint by maintaining a local concentration that is lethal to marine organisms. However, over a period of time, the effect of these anti-biofouling agents and fungicides reduce due to leaching, and the coating becomes ineffective. Accordingly, paints and coatings with better hydrophilic and biocidal properties are desirable.

The present disclosure is directed to paints and compounds that provide hydrophilic and biocidal properties when incorporated in a paint. The compounds can be added as an additive in paints or can be polymerized with acrylates to form a binder. In some embodiments, the compound is of formula I where E may be phosphorus, bismuth, arsenic or vanadium. $R_1$ may be a quaternary amine polyethylene glycol group and is represented by the formula where A may be alkyl, substituted alkyl, cycloalkyl, heteroalkyl, aryl, heteroaryl or substituted aryl. $R_2$ in formula I is —$CH_2$— or —$CH(-CH_3)$—. $R_3$ may be a polyaminoalkyl biguanide group and is represented by the formula where n is an integer from 2 to 20. $R_4$ may be H, vinyl, propenyl, butenyl, pentenyl, or hexenyl.

The compound of formula I described herein imparts hydrophilic, self-cleaning and biocidal properties when incorporated in a paint. For example, the polyethylene glycol units contribute to the hydrophilicity because of the ether linkages of polyethylene glycol forming hydrogen bonds with a water molecule. The polyethylene glycol may be 2 to 25 units in length, in some embodiments. Polyaminoalkyl biguanides contribute to the biocidal property of the compound. Their incorporation in paints serves the dual purpose of providing both hydrophilicity and biocidal behavior, which could be useful when combating the growth of mold and microbes. The biguanides may incorporate themselves into the cell membranes of bacteria, cause DNA damage, and ultimately kill the microbe.

In some embodiments, the compound of formula I may also be hydrophobic depending on the substitutions in the quaternary amine group. For example, the quaternary amine may have an alkyl substitution of about 2 to 24 C atoms in length, thus imparting a hydrophobic property to the compound. The hydrophobic or hydrophilic property of the compound may be altered by modifying the length of the alkyl and polyethylene glycol chain lengths.

In some embodiments, the compound of formula I may have the following substitutions at $R_1$, $R_2$, $R_3$, $R_4$ and E, as shown in Table 1.

TABLE 1

| $R_1$ | $R_2$ | $R_3$ | $R_4$ | E |
|---|---|---|---|---|
| (alkyl)$_3$-N$^+$(CH$_2$CH$_2$O)$_{20}$— | —CH$_2$— | Polyaminopropyl biguanide | H | phosphorus |
| (aryl)$_3$-N$^+$(CH$_2$CH$_2$O)$_{20}$— | —CH$_2$— | Polyaminopropyl biguanide | H | phosphorus |
| (substituted alkyl)$_3$-N$^+$(CH$_2$CH$_2$O)$_{20}$— | —CH$_2$— | Polyaminopropyl biguanide | H | phosphorus |
| (hetero alkyl)$_3$-N$^+$(CH$_2$CH$_2$O)$_{20}$— | —CH$_2$— | Polyaminopropyl biguanide | H | phosphorus |
| (cyclo alkyl)$_3$-N$^+$(CH$_2$CH$_2$O)$_{20}$— | —CH$_2$— | Polyaminopropyl biguanide | H | phosphorus |
| (substituted aryl)$_3$-N$^+$(CH$_2$CH$_2$O)$_{20}$— | —CH$_2$— | Polyaminopropyl biguanide | H | phosphorus |
| (hetero aryl)$_3$-N$^+$(CH$_2$CH$_2$O)$_{20}$— | —CH$_2$— | Polyaminopropyl biguanide | H | phosphorus |
| (alkyl)$_3$-N$^+$(CH$_2$CH$_2$O)$_{20}$— | —CH(—CH$_3$)— | Polyaminopropyl biguanide | H | phosphorus |
| (aryl)$_3$-N$^+$(CH$_2$CH$_2$O)$_{20}$— | —CH(—CH$_3$)— | Polyaminopropyl biguanide | H | phosphorus |
| (substituted alkyl)$_3$-N$^+$(CH$_2$CH$_2$O)$_{20}$— | —CH(—CH$_3$)— | Polyaminopropyl biguanide | H | phosphorus |
| (hetero alkyl)$_3$-N$^+$(CH$_2$CH$_2$O)$_{20}$— | —CH(—CH$_3$)— | Polyaminopropyl biguanide | H | phosphorus |
| (cyclo alkyl)$_3$-N$^+$(CH$_2$CH$_2$O)$_{20}$— | —CH(—CH$_3$)— | Polyaminopropyl biguanide | H | phosphorus |
| (substituted aryl)$_3$-N$^+$(CH$_2$CH$_2$O)$_{20}$— | —CH(—CH$_3$)— | Polyaminopropyl biguanide | H | phosphorus |
| (hetero aryl)$_3$-N$^+$(CH$_2$CH$_2$O)$_{20}$— | —CH(—CH$_3$)— | Polyaminopropyl biguanide | H | phosphorus |
| (alkyl)$_3$-N$^+$(CH$_2$CH$_2$O)$_{20}$— | —CH$_2$— | Polyaminopropyl biguanide | vinyl | phosphorus |
| (aryl)$_3$-N$^+$(CH$_2$CH$_2$O)$_{20}$— | —CH$_2$— | Polyaminopropyl biguanide | vinyl | phosphorus |

TABLE 1-continued

| R$_1$ | R$_2$ | R$_3$ | R$_4$ | E |
|---|---|---|---|---|
| (substituted alkyl)$_3$-N$^+$(CH$_2$CH$_2$O)$_{20}$— | —CH$_2$— | Polyaminopropyl biguanide | vinyl | phosphorus |
| (hetero alkyl)$_3$-N$^+$(CH$_2$CH$_2$O)$_{20}$— | —CH$_2$— | Polyaminopropyl biguanide | vinyl | phosphorus |
| (cyclo alkyl)$_3$-N$^+$(CH$_2$CH$_2$O)$_{20}$— | —CH$_2$— | Polyaminopropyl biguanide | vinyl | phosphorus |
| (substituted aryl)$_3$-N$^+$(CH$_2$CH$_2$O)$_{20}$— | —CH$_2$— | Polyaminopropyl biguanide | vinyl | phosphorus |
| (hetero aryl)$_3$-N$^+$(CH$_2$CH$_2$O)$_{20}$— | —CH$_2$— | Polyaminopropyl biguanide | vinyl | phosphorus |
| (alkyl)$_3$-N$^+$(CH$_2$CH$_2$O)$_{20}$— | —CH(—CH$_3$)— | Polyaminopropyl biguanide | vinyl | phosphorus |
| (aryl)$_3$-N$^+$(CH$_2$CH$_2$O)$_{20}$— | —CH(—CH$_3$)— | Polyaminopropyl biguanide | vinyl | phosphorus |
| (substituted alkyl)$_3$-N$^+$(CH$_2$CH$_2$O)$_{20}$— | —CH(—CH$_3$)— | Polyaminopropyl biguanide | vinyl | phosphorus |
| (hetero alkyl)$_3$-N$^+$(CH$_2$CH$_2$O)$_{20}$— | —CH(—CH$_3$)— | Polyaminopropyl biguanide | vinyl | phosphorus |
| (cyclo alkyl)$_3$-N$^+$(CH$_2$CH$_2$O)$_{20}$— | —CH(—CH$_3$)— | Polyaminopropyl biguanide | vinyl | phosphorus |
| (substituted aryl)$_3$-N$^+$(CH$_2$CH$_2$O)$_{20}$— | —CH(—CH$_3$)— | Polyaminopropyl biguanide | vinyl | phosphorus |
| (hetero aryl)$_3$-N$^+$(CH$_2$CH$_2$O)$_{20}$— | —CH(—CH$_3$)— | Polyaminopropyl biguanide | vinyl | phosphorus |

In some embodiments, a method for making the compound of formula I may include: (a) contacting an inorganic halide with an end-capped polyethylene glycol and an amino acid to form an intermediate compound; and (b) contacting the intermediate compound with a poly aminoalkyl biguanide to form the biocidal compound. Non-limiting examples of inorganic halides may be a phosphorus halide, a bismuth halide, an arsenic halide or a vanadium halide. The end-capped polyethylene glycol may be a quaternary amine polyethylene glycol represented by the formula where A is alkyl, substituted alkyl, cycloalkyl, heteroalkyl, aryl, heteroaryl or substituted aryl. The amino acid used in some embodiments may be serine, threonine, a serine derivative or a threonine derivative. The step may include contacting the inorganic halide, end-capped polyethylene glycol and the amino acid in the presence of a weak base. The base, for example, may be 2,6-lutidine, di-isopropyl ethylene amine, or pyridine. This reaction step may be performed at a temperature of about 0° C. to about 4° C., of about 0° C. to about 3° C., or of about 0° C. to about 1° C. Specific examples also include about 0° C., about 1° C., about 2° C., about 3° C., about 4° C., and ranges between (and including the endpoints of) any two of these values. This contacting step results in the formation of an intermediate cyclic compound, as represented by formula II:

where E is phosphorus, bismuth, arsenic or vanadium; R$_1$ is where A is alkyl, substituted alkyl, cycloalkyl, heteroalkyl, aryl, heteroaryl or substituted aryl; and R$_2$ is —CH$_2$— or —CH(—CH$_3$)—.

Figure 1:
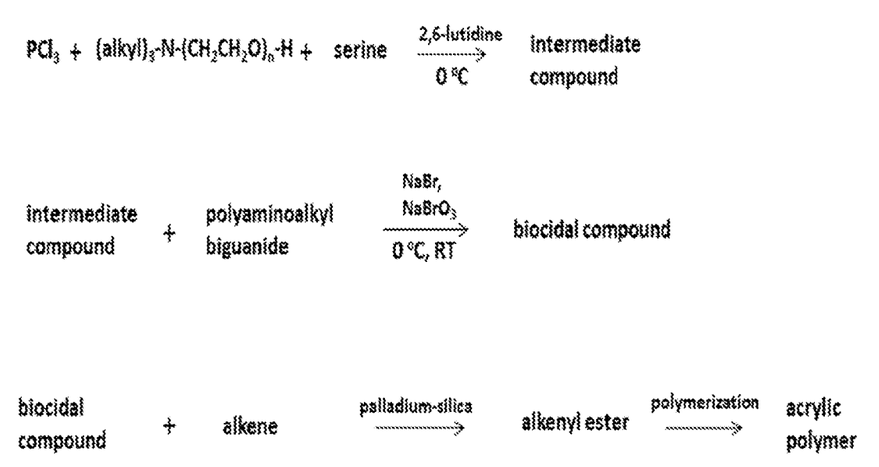
FIG. 1 outlines the preparation of a hydrophilic, biocidal compound according to an embodiment.

Another step may include contacting the intermediate compound of formula II with a polyaminoalkyl biguanide in the presence of an oxidant. The polyaminoalkyl biguanide is represented by the formula wherein n is an integer from 2 to 20. Examples of oxidants that may be used include hypochlorite, a bromide, an iodide, a peroxymonosulfate, a bromate or a combination thereof. This reaction step may be performed at a temperature of about 0° C. to about 30° C., of about 0° C. to about 25° C., of about 0° C. to about 10° C., or of about 0° C. to about 5° C. Specific examples also include about 0° C., about 5° C., about 10° C., about 15° C., about 20° C., about 30° C., and ranges between (and including the endpoints of) any two of these values. The oxidation step opens the cyclic intermediate compound and causes the biguanide group to react with the inorganic compound E. The resulting product formed out of this reaction is the compound of formula I described herein, wherein $R_4$ is H. The steps of the reaction are outlined in FIG. 1.

In some embodiments, the hydrophilic, biocidal compound of formula I may be used as a paint additive and dispersed in one or more organic binders, such as a polymeric organic binder. It is contemplated that any polymeric binder may be employed. In some embodiments, the polymeric binder is a water-dispersible polymer. The water-dispersible polymer may include, for example, a latex binder, such as natural latex, neoprene latex, nitrile latex, acrylic latex, vinyl acrylic latex, styrene acrylic latex, styrene butadiene latex, or the like. Compositions may also include a single binder or a mixture of two or more polymeric binders that may be of the same class or different classes. For example, organic binders may be combined with a silicon-based binder.

In some embodiments, the compound of formula I may be dispersed in one or more inorganic binders. Inorganic binders may include, without limitation, alkali metal silicates, such as potassium silicate, sodium silicate, lithium silicate, or the like.

The compounds of formula I may be added to a paint composition during any step of the paint preparation or before a consumer uses the paint. The compounds of formula I may be present as a separate component or a kit, and mixed with the paint before use. For example, the end consumer may add the compound to any conventional paint formulation before use.

The compound of formula I may be present in a paint formulation at about 0.5 to about 40 weight percent, at about 0.5 weight percent to about 20 weight percent, at about 0.5 weight percent to about 10 weight percent, at about 0.5 weight percent to about 5 weight percent, or at about 0.5 weight percent to about 1 weight percent. Additional examples include about 0.5 weight percent, about 0.7 weight percent, about 1 weight percent, about 2 weight percent, about 5 weight percent, about 10 weight percent, about 15 weight percent, about 30 weight percent, about 40 weight percent of the total weight, and ranges between (including the endpoints of) any two of these values.

In some embodiments, the compound of formula I may be coupled to an alkene at $R_4$ position to form an alkenyl ester. The $R_4$ substitution may be vinyl, propenyl, butenyl, pentenyl, or hexenyl. The presence of an alkenyl group may aid in polymerizing the compound of formula I with acrylates, resulting in a polymer/binder with hydrophilic, self-cleaning and biocidal properties. The monomer compound of formula I may be polymerized with acrylates using an emulsion polymerization process. Examples of acrylates include, but are not limited to, alkyl methacrylates, allyl methacrylates, acrylic acid, methacrylic acid, acrylamide, 2-hydroxyethyl methacrylate, 2-hydroxypropyl methacrylate, thioethyl methacrylate, vinyl methacrylate, 2-hydroxyethyl acrylate, butyl acrylate, 2-ethylhexyl acrylate, and combinations thereof.

A typical emulsion polymerization process involves heating a mixture containing water, an initiator, and a surfactant and adding the biocidal compound of formula I and acrylates dropwise with constant stirring. The initiator/surfactant mixture and acrylate/biocidal compound mixture are vigorously mixed to form micelles. The rate at which the acrylate/biocidal compound mixture is added may be varied to obtain micelles of different sizes which influence film formation. In some embodiments, the mixture is heated to a temperature of about 50° C. to about 95° C., about 50° C. to about 80° C., or about 50° C. to about 70° C. Specific examples include about 50° C., about 60° C., about 70° C., about 74° C., about 80° C., about 95° C., and ranges between (and including the endpoints of) any two of these values. The mixing process may be performed for generally any length of time, including about 1 hour to about 12 hours, for about 1 hour to about 8 hours, for about 1 hour to about 6 hours, or for about 1 hour to about 4 hours. Specific examples include about 1 hour, about 2 hours, about 4 hours, about 6 hours, about 7 hours, about 8 hours, about 9 hours, about 12 hours, and ranges between (an including the endpoints of) any two of these values. Some of the surfactants that may be used in the process are dodecyl sulfate, alkyl phenol ethoxylate, sodium lauryl sulfate, dodecylbenzene sulfonate, polyoxyethylene alkyl ethers, polyoxyethylene alkyl allyl ethers, acetylene glycols, polyoxyethylene, polyoxypropylene or any combination thereof. Examples of initiators that may be used include, but are not limited to, benzoyl peroxide, persulfates, water soluble azo initiators, water soluble peroxides, a persulfate redox systems or any combination thereof. The resulting product is an emulsion containing polymer particles suspended in water.

Paints and coatings may contain one or more additives in their composition. These additives may alter one or more of the properties of the paint, such as shelf life, application, longevity, and health and safety. Such additives may be added, for example, during the manufacture of the emulsion polymer or during the formulation of the paint itself. Additives include, but are not limited to, initiators, rheology modifiers, preservatives, coalescing agents, and the like. Initiators are a source of free radicals to initiate the polymerization process in which monomers condense to form the polymers. Coatings may contain a redox system initiator, such as ferrous and thiosulfate salts along with the persulfate salts, that promote polymerization at room temperature.

Thickeners and rheology modifiers may be also be added to coatings to achieve the desired viscosity and flow properties. Thickeners function by, for example, forming multiple hydrogen bonds with the acrylic polymers, thereby causing chain entanglement, looping and/or swelling which results in volume restriction. Thickeners, such as cellulose derivatives including hydroxyethyl cellulose, methyl cellulose and carboxymethyl cellulose, may be used in the compositions.

One or more preservatives may be added in the coating compositions in low doses to protect against the growth of microorganisms. Preservatives, such as methyl benzisothiazolinones, chloromethylisothiazolinones, barium metaborate and 1-(3-chloroallyl)-3,5,7-triaza-1-azoniaadamantane chloride, may be used.

Coalescing agents, such as ester alcohols, benzoate ethers, glycol ethers, glycol ether esters and n-methyl-2-pyrrolidone, may be added to the coating compositions. Coalescing agents are added, for example, to promote film formation under varying atmospheric conditions. They may be slow evaporating solvents with some solubility in the polymer phase. They may also act as a temporary plasticizer, allowing film formation at temperatures below the system's glass transition temperature. After film formation, the coalescing agents may slowly diffuse to the surface and evaporate, increasing the hardness and block resistance of the film.

Coatings may further contain one or more of the following additives: solvents, pigments, plasticizers, surfactants, and the like. Surfactants may be used, for example, to create the micelles for particle formation, as well as long-term particle stabilization, to provide stability through electrostatic and steric hindrance mechanisms. Both ionic and non-ionic surfactants may be used. Examples may include, but are not limited to, alkyl phenol ethoxylates, sodium lauryl sulfate, dodecylbenzene sulfonate, polyoxyethylene alkyl ethers, polyoxyethylene alkyl allyl ethers, acetylene glycols, polyoxyethylene, stearic acid and polyoxypropylene.

One or more plasticizers may be added to the compositions to adjust the tensile properties of the paint film. Plasticizers include, for example, a glucose-based derivative, a glycerine-based derivative, propylene glycol, ethylene glycol, phthalates and the like.

Paints may further include one or more pigments. The term "pigments" is intended to embrace, without limitation, pigmentary compounds employed as colorants, including white pigments, as well as ingredients commonly known in the art as "opacifying agents" and "fillers". Pigments may be any particulate organic or inorganic compound and may provide coatings the ability to obscure a background of contrasting color (hiding power).

The coating of the present disclosure may be a decorative coating, an industrial coating, a protective coating, a self-cleaning coating, or any combination thereof. The coating of the present disclosure may generally be applied to any substrate. The substrate may be an article, an object, a vehicle, or a structure. Although no particular limitation is imposed on the substrate to be used in the present disclosure, exemplary substrates include, an exterior of a building, vehicles, bridges, airplanes, hull of a boat or ship, metal railings, fences, glasses, plastics, metals, ceramics, wood, stone, cement, fabric, paper, leather, surfaces of swimming pools, spas, showers, bathtubs, sinks, ceramic and porcelain tile, plumbing, faucets, shower curtains, pipes, drains and sewers, electronics, automotive parts, marine parts, aerospace parts and other metal substrates. The coating may be applied to a substrate by generally any method, such as spraying, dipping, rolling, brushing, or any combination thereof.

Biocidal compounds described herein may also be applied as a powder or a solution to control the growth of microbes on wood, plastics, biofuels, garbage cans, and adsorbents. The biocidal compounds described herein may also be used in water treatment plants, swimming pools, aquariums, toilets, hospitals, food processing industries, restaurants, waste management industries and the like.

EXAMPLES

Example 1

Preparation of a Biocidal Compound

About 0.35 mL of phosphorus trichloride (4.0 mmol, 1.3 equivalents) is dissolved in 8 mL of tetrahydrofuran (THF) and the mixture is cooled down to about 0-5° C. using an external ice/water bath. $PEG_{3000}$ (1.5 equivalents) is added slowly to this mixture and temperature of the reaction is maintained below 5° C. The solution is stirred for 5 minutes around 0-5° C. and the consumption of $PCl_3$ is monitored by $^{31}P$ NMR analysis in $CDCl_3$. Next, about 1.06 mL of 2,6-Lutidine (9.13 mmol, 3.00 equivalents) is added to the flask slowly while maintaining the reaction temperature between −5° C. and 5° C.

In a separate flask, about 0.36 mL of 2,6-lutidine (3.1 mmol, 1.0 equivalents) is added to a solution of serine (3.05 mmol, 1.00 equivalents) in THF (4.0 mL). This solution is added slowly to the above phosphorus trichloride-$PEG_{300}$ mixture at a rate such that the reaction temperature is maintained between −5° C. and 5° C. Aliquots are removed at intervals and examined by HPLC to confirm the completion of the reaction. To this, about 1.5 equivalents of polyaminopropyl biguanide is added, taking care to maintain the temperature of the reaction mixture below 10° C. This followed by addition of NaBr (0.73 grams, 7.1 mmol, 2.3 equivalents) at about 0° C. Next, an aqueous solution of $NaBrO_3$ (0.22 grams, 1.5 mmol, 0.48 equivalents in 20% water) is added slowly keeping the reaction temperature at about 0-5° C. After the addition is complete, the cooling bath is removed and the reaction is allowed to warm to room temperature. The completion of the reaction is monitored by HPLC, and at the end of the reaction an aqueous solution of $Na_2S_2O_5$ (1.0 mL) is added to the flask in one portion to consume any remaining oxidant. About 10 mL of ethyl acetate is then added and mixed well. The organic layer is washed with saturated aqueous NaCl (10 mL), dried with anhydrous magnesium sulfate (1.00 grams) and filtered. The filtrate is examined by HPLC against an external standard to obtain the crude product. The product is isolated by concentrating the organic layer to an oil, diluting with ethyl acetate (7 mL/grams), and stirring at ambient temperature overnight and then filtering at −10° C. to obtain the biocidal compound.

Example 2

Coupling Biocidal Compound to an Alkene

Preparation of the catalyst: 1.2 liters of a silica support in the form of 5 millimeter diameter spheres, having a density of 540 grams per liter and a pore volume of 0.68 ml per gram of support and having a pH of 4.0 in a 10% by weight water suspension is impregnated with 440 ml of an aqueous solution of $Na_2PdCl_4$ and $HAuCl_4$ containing 3.96 grams palladium and 1.8 grams of gold (which represents 99.8% of absorptive capacity of the support). A container holding this mixture is rotated mechanically until the solution is completely absorbed by the silica spheres. To this, about 500 ml of a solution containing 25.2 grams of sodium metasilicate ($Na_2SiO_3$ nonahydrate) is added. After standing for 12 hours at room temperature, about 25 ml of 85% hydrazine hydrate is added, mixed gently and allowed to stand for 4 hours at room temperature in order to reduce the palladium and gold salts down to the base metals. The catalyst is then washed with distilled water three times (decantation) followed by a continuous wash for 16 hours at the rate of 1-2 liters of distilled water per hour. The catalyst is then dried at 110° C. for 4 hours, cooled, impregnated with a solution containing 36 grams of potassium acetate (corresponding to 30 grams of potassium acetate per liter of catalyst) and re-dried.

The catalyst prepared above is filled in a reaction tube measuring 2 meters in length with an inside diameter of 25 mm. Ethylene (70 moles per hour), oxygen (5.25 mols per hour) and biocidal compound (17.1 moles per hour) of Example 1 is fed into the reaction tube. The jacket of the reactor is heated to 150° C. under a pressure of 120 psig. The product is washed free of the silica catalyst with ethyl acetate, then evaporated to dryness to yield the ester product.

Example 3

Preparation of a Hydrophilic Coating Containing a Biocidal Compound

A hydrophilic coating is prepared having the following components: 40 grams of chromium oxide pigment, 2 grams of biocidal compound (Example 1), 2 grams of thickener (hydroxyethyl cellulose), 150 grams of solvent (water), 70 grams of binder (methyl methacrylate), and 0.3 grams of coalescing agent (2,2,4-trimethyl-1,3-pentanediolmono(2-methylpropanoate)). The components are mixed under high shear for 30 minutes.

Example 4

Emulsion Polymerization

The reaction process has the following components: a pre-emulsion mix containing 100 grams of the ester compound of Example 2, 250 grams of methacrylate, 3 grams of nonylphenol polyglycol ether, 0.66 grams of nonylphenol polyglycol ether sodium sulfate, 75 grams of water and 0.91 grams of lauryl mercaptan; and an initiator/surfactant mix containing 16 grams of nonylphenol polyglycol ether, 3.14 grams of nonylphenol polyglycol ether sodium sulfate, 1 grams of polyvinyl alcohol, 1.35 grams of sodium bicarbonate, 30 grams of tert-butyl hydroperoxide, 33.8 grams of formaldehyde sulphoxylate and 100 grams of water. The initiator/surfactant mix is pre-heated to a temperature of about 74° C. in a jacketed glass reactor and the pre-emulsion mix is slowly added dropwise with constant vigorous mixing. The reaction temperature is slowly raised to 90° C., and the mixing is performed for 6 hours. The resulting emulsion is cooled.

Example 5

Evaluation of Hydrophilic Property

The hydrophilic coating containing the polymer of Example 4 is coated on a glass surface and dried at room temperature. The surface free energy and the water droplet contact angle of the hydrophilic coating is measured as follows. A Zisman plotting method is employed for measuring the surface free energy. The surface tension of various concentrations of the aqueous solution of magnesium chloride is plotted along the X-axis, and the contact angle in terms of cos θ is plotted along the Y-axis. A graph with a linear relationship between the two is obtained. The graph is extrapolated such that the surface tension at contact angle 0° is measured and is defined as the surface free energy of the solid. The surface free energy of the glass surface measured will be 81 milliNewton/meter.

Example 6

An Object Coated with Hydrophilic Paint

A metal table is painted with a hydrophilic coating containing the compound of Example 1 and is allowed to dry at room temperature. The surface free energy of the chair is measured as explained in Example 4 and will be 81 milliNewton/meter. The anti-fouling property of the coating is measured as follows: A line is drawn on the coated table using oily ink. A similar line is also drawn on a table which is not coated. A water jet is continuously applied on both the surfaces and periodically checked to determine whether the oily line is erased. The oily ink applied on the coated table will be erased after 1 minute whereas the oily line on the un-coated table will be un-changed and visible.

Example 7

Anti-Fouling Properties

A hydrophilic coating with a biocidal compound of Example 1 is coated on a wooden surface. A similar wooden surface is coated with a paint without the biocidal compound. After drying the paint, the surfaces are exposed to running water for one month. At the end of the period, the wooden surfaces are checked for visible peeling of the paint and growth of organisms such as algae. The wooden surface coated with the paint containing the biocidal compound will be free of algae, while the other surface will exhibit the growth of algae.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having"

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A compound having the formula I wherein E is phosphorus, bismuth, arsenic or vanadium;
$R_1$ is wherein A is alkyl, substituted alkyl, cycloalkyl, heteroalkyl, aryl, heteroaryl or substituted aryl;
$R_2$ is —$CH_2$— or —CH(—$CH_3$)—;
$R_3$ is wherein n is an integer from 2 to 20; and
$R_4$ is H, vinyl, propenyl, butenyl, pentenyl, or hexenyl.

2. The compound of claim 1, wherein
E is phosphorus;
$R_1$ is $R_2$ is —$CH_2$—;
$R_3$ is polyaminopropyl biguanide; and
$R_4$ is vinyl.

3. A method of making a biocidal compound of formula I, wherein E is phosphorus, bismuth, arsenic or vanadium;
R₁ is wherein A is alkyl, substituted alkyl, cycloalkyl, heteroalkyl, aryl, heteroaryl, or substituted aryl;
R₂ is —CH₂— or —CH(—CH₃)—;
R₃ is wherein n is an integer from 2 to 20; and
R₄ is H, vinyl, propenyl, butenyl, pentenyl, or hexenyl;
the method comprising;
contacting an inorganic halide with an end-capped quaternary amine polyethylene glycol of the following formula:

wherein A is alkyl, substituted alkyl, cycloalkyl, heteroalkyl, aryl, heteroaryl or substituted aryl; and an amino acid to form an intermediate compound; and
contacting the intermediate compound with a polyaminoalkyl biguanide of the following formula:

wherein n is an integer from 2 to 20;
to form the biocidal compound.

4. The method of claim 3, wherein the inorganic halide is a halide of phosphorus, bismuth, arsenic or vanadium.

5. The method of claim 3, wherein the amino acid is serine, threonine or its derivatives.

6. The method of claim 3, wherein contacting the inorganic halide with the end-capped polyethylene glycol and the amino acid comprises contacting the inorganic halide, the end-capped polyethylene glycol and the amino acid in the presence of a weak base.

7. The method of claim 3, wherein contacting the intermediate compound with the polyaminoalkyl biguanide comprises contacting the intermediate compound and the polyaminoalkyl biguanide in the presence of an oxidant.

8. The method of claim 3, wherein contacting the intermediate compound with the polyaminoalkyl biguanide comprises contacting the intermediate compound and the polyaminoalkyl biguanide at a temperature of about 0° C. to about 30° C.

9. A method of making a paint polymer, the method comprising:
contacting an inorganic halide with an end-capped quaternary amine polyethylene glycol of the following formula:

wherein A is alkyl, substituted alkyl, cycloalkyl, heteroalkyl, aryl, heteroaryl or substituted aryl;
and an amino acid
to form an intermediate compound; and contacting the intermediate compound with a polyaminoalkyl biguanide of the following formula:

wherein n is an integer from 2 to 20;
to form a biocidal compound;
contacting the biocidal compound with an alkene to form a monomer having the formula I:

wherein E is phosphorus, bismuth, arsenic or vanadium;
R₁ is wherein A is alkyl, substituted alkyl, cycloalkyl, heteroalkyl, aryl, heteroaryl, or substituted aryl;

R₂ is —CH₂— or —CH(—CH₃)—;
R₃ is wherein n is an integer from 2 to 20; and
R₄ is vinyl, propenyl, butenyl, pentenyl, or hexenyl;
and incorporating the monomer into a polymer to form a paint.

10. The method of claim 9, wherein the inorganic halide is a halide of phosphorus, bismuth, arsenic or vanadium.

11. The method of claim 9, wherein the amino acid is serine, threonine or its derivatives.

12. The method of claim 9, wherein the alkene is ethylene, propene, butene, pentene or hexene.

13. The method of claim 9, wherein contacting the inorganic halide with the end-capped polyethylene glycol and the amino acid comprises contacting the inorganic halide, the end-capped polyethylene glycol and the amino acid in the presence of a weak base.

14. The method of claim 9, wherein contacting the intermediate compound with the polyaminoalkyl biguanide comprises contacting the intermediate compound and the polyaminoalkyl biguanide in the presence of an oxide.

15. The method of claim 9, wherein contacting the intermediate compound with the polyaminoalkyl biguanide comprises contacting the intermediate compound and the polyaminoalkyl biguanide at a temperature of about 0° C. to about 30° C.

16. The method of claim 9, wherein incorporating the monomer comprises copolymerizing the monomer with an acrylate to form the polymer.

17. A coating composition comprising:
an acrylic polymer comprising a monomeric unit of formula I wherein E is phosphorus, bismuth, arsenic or vanadium;
R₁ is wherein A is alkyl, substituted alkyl, cycloalkyl, heteroalkyl, aryl, heteroaryl or substituted aryl;
R₂ is —CH₂— or —CH(—CH₃)—;
R₃ is wherein n is an integer from 2 to 20; and
R₄ is vinyl, propenyl, butenyl, pentenyl, or hexenyl.

18. The composition of claim 17, wherein the acrylic polymer is an alkyl methacrylate polymer, an allyl methacrylate polymer, a thioethyl methacrylate polymer, vinyl methacrylate polymer, vinyl benzene polymer, 2-hydroxyethyl acrylate polymer, butyl acrylate polymer, 2-ethylhexyl acrylate polymer or a combination thereof.

19. The composition of claim 17, wherein the coating is configured to provide a hydrophilic, self-cleaning and biocidal property when applied on a substrate.

\* \* \* \* \*

UNITED STATES PATENT AND TRADEMARK OFFICE
CERTIFICATE OF CORRECTION

PATENT NO. : 8,785,679 B2  Page 1 of 1
APPLICATION NO. : 13/881540
DATED : July 22, 2014
INVENTOR(S) : Brizius et al.

It is certified that error appears in the above-identified patent and that said Letters Patent is hereby corrected as shown below:

In the Claims

In Column 17, Line 36, in Claim 3, delete "comprising;" and insert -- comprising: --, therefor.

In Column 18, Line 30, in Claim 9, delete "to form an intermediate compound; and" and insert the same at Line 29, after "acid" as a continuation subpoint.

In Column 18, Lines 35-37, in Claim 9, delete " " and insert -- -- , therefor.

In Column 19, Line 14, in Claim 9, delete "and" and insert the same at Line 13, after "hexenyl;" as a continuation subpoint.

Signed and Sealed this
Third Day of February, 2015

Michelle K. Lee
*Deputy Director of the United States Patent and Trademark Office*